(12) United States Patent
Widengren

(10) Patent No.: US 7,839,500 B2
(45) Date of Patent: Nov. 23, 2010

(54) APPARATUS, METHOD AND COMPUTER PROGRAM FOR SPECTROSCOPIC MEASUREMENTS AND ANALYSIS

(76) Inventor: Jerker Widengren, Årebacken 8, Solna SE-169 54 (SE)

( * ) Notice: Subject to any disclaimer, the term of this patent is extended or adjusted under 35 U.S.C. 154(b) by 326 days.

(21) Appl. No.: 11/920,789

(22) PCT Filed: May 29, 2006

(86) PCT No.: PCT/SE2006/050163

§ 371 (c)(1),
(2), (4) Date: Nov. 20, 2007

(87) PCT Pub. No.: WO2006/130105

PCT Pub. Date: Dec. 7, 2006

(65) Prior Publication Data

US 2009/0040518 A1 Feb. 12, 2009

Related U.S. Application Data

(60) Provisional application No. 60/595,021, filed on May 30, 2005.

(30) Foreign Application Priority Data

May 30, 2005 (SE) .................................. 0501215
Dec. 23, 2005 (SE) .................................. 0502922

(51) Int. Cl.
*G01N 21/64* (2006.01)
(52) U.S. Cl. ..................... 356/318; 356/417; 250/458.1
(58) Field of Classification Search ................. 356/317, 356/318
See application file for complete search history.

(56) References Cited

U.S. PATENT DOCUMENTS 5,323,008 A 6/1994 Studholme et al.
6,816,256 B1 11/2004 Lloyd (Continued)

FOREIGN PATENT DOCUMENTS

EP 0515211 A2 11/1992

OTHER PUBLICATIONS

"PCT Application No. PCT/SE2006/050163, International Search Report mailed Aug. 17, 2006", 3 pgs.

(Continued)

*Primary Examiner*—F. L Evans
(74) *Attorney, Agent, or Firm*—Schwegman, Lundberg & Woessner, P.A.

(57) ABSTRACT

The present invention relates to a spectroscopic method and associated apparatus and computer program for measuring and analysing intensities of fluorescent molecules excited by an energy pulse. The method includes the steps of: a) generating a transient state build-up in the fluorescent molecules by means of an excitation pulse, within which pulse repetitive excitation-emission cycles are induced in the fluorescent molecules between their ground, typically singlet (So) and excited, typically singlet (SO states, resulting also in transition from S] to the transient state, b) relaxation of population of the transient state by transition back to the ground state in a time period following directly after the excitation pulse, c) determination of the transient state population by recording the fluorescence. The invention is characterised by varying pulse characteristics from one sequence of pulses to the next so as to circumvent the need of time-resolution in the detection.

47 Claims, 13 Drawing Sheets

U.S. PATENT DOCUMENTS

Figure 1:
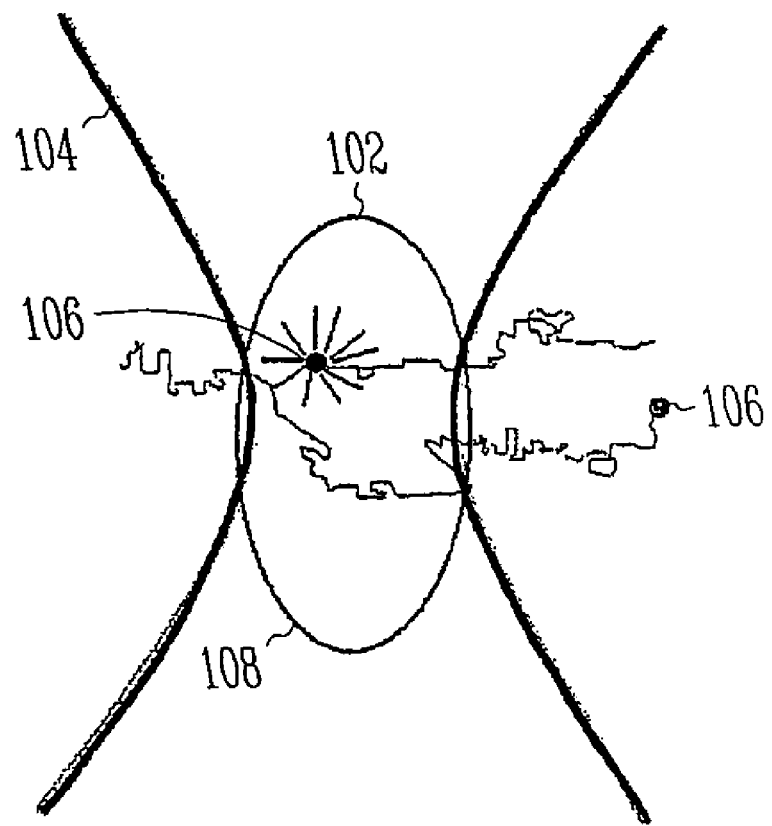

2003/0058440 A1   3/2003   Scott et al.

OTHER PUBLICATIONS

"PCT Application No. PCT/SE2006/050163, Written Opinion mailed Aug. 17, 2006", 5 pgs.

Auer, M., et al., "Fluororescence correlation spectroscopy: lead discovery by miniaturized HTS", *Drug Discovery Today*, 3(10), (Oct. 1998), 457-465.

Eggeling, C., et al., "Highly sensitive fluorescence detection technology currently available for HTS", *Drug Discovery Today*, 8(14), (Jul. 2003), 632-641.

Förster, T., "Zwischenmolekulare Energiewanderung und Fluoreszenz [Intermolecular Energy Transfer and Fluorescence]", *Annalen der Physik*, 437(Issue 1-2), (1948), 55-75.

Hörber, J. K. H., et al., "Scanning Probe Evolution in Biology", *Science*, 302(5647), (2003), 1002-1005.

Jalili, N., et al., "A review of atomic force microscopy imaging systems: application to molecular metrology and biological sciences", *Mechatronics*, 14(8), (Oct. 2004), 907-945.

Jares-Erijman, E. A., et al., "FRET imaging", *Nature Biotechnology*, 21(11), (Nov. 2003), 1387-1395.

Stryer, L., et al., "Energy TransferL A Spectroscopic Ruler", *Proc. Natl. Acad. Sci.*, 58(2), (1967), 719-726.

Widengren, J., et al., "Chapter 3—Conceptual Basic of Fluorescence Correlation Spectroscopy and Related Techniques as Tools in Bioscience", *In: Single Molecular Detection in Solution—Methods and Applications*, Wiley-VCH Verlag, Berlin GmbH, Berlin, Germany, (2002), 69-120.

Widengren, J., et al., "Characterization of Photoinduced Isomerization and Back-Isomerization of the Cyanine Dye Cy5 by Fluorescene Correction Spectroscopy", *J. Phys. Chem. A*, 104(27), (2000), 6416-6428.

Widengren, J., et al., "Fast interactions between Rh6G and dGTP in water studied by fluorescence correlation spectroscopy", *Chemical Physics*, 216(3), (1997), 417-426.

Widengren, J., et al., "Fluorescence Correlation Spectroscopy of Triplet States in Solution: A Theorectical and Experimental Study", *Journal of Physical Chemistry*, 99(36), (1995), 13368-13379.

Widengren, J., et al., "Manipulation and characterization of photoinduced transient states of Merocyanine 540 by fluorescence correlation spectroscopy", *Physical Chemistry Chemical Physics*, 2(15), (2000), 3435-3441.

APPARATUS, METHOD AND COMPUTER PROGRAM FOR SPECTROSCOPIC MEASUREMENTS AND ANALYSIS

RELATED APPLICATIONS

This application is a nationalization under 35 U.S.C. 371 of PCT/SE2006/050163, filed May 29, 2006 and published as WO 2006/130105 A1 on Dec. 7, 2006, which claimed priority under 35U.S.C. 119 to Sweden Patent Application Serial No. 0501215-8, filed May 30, 2005; Sweden Patent Application Serial No. 0502922-8, filed Dec. 23, 2005; and which claimed priority under 35 U.S.C. 119(e) to U.S. Provisional Patent Application Ser. No. 60/595,021, filed May 30, 2005; which applications and publication are incorporated herein by reference and made a part hereof.

TECHNICAL FIELD OF THE INVENTION

The present invention relates to an apparatus, spectroscopic method and a related computer program for measuring and analysing intensities of fluorescent molecules excited by an energy pulse. More in detail, the invention relates to generation of a transient state build-up in a fluorescent material by means of an excitation pulse, and relaxation back to ground state in a time period with no excitation. The transient-state properties are determined from the dependence of fluorescence intensity on the durations of periods with and without excitation.

BACKGROUND OF THE INVENTION

There are several known ways of measuring and obtaining characteristics and various transient-state properties in fluorescent molecules. One way is the so-called fluorescence correlation spectroscopy (FCS) (see J. Widengren and Ü. Mets p. 69-119 in "Single Molecule Detection in Solution—methods and applications" VCH-Wiley Verlag, Berlin, 2002). The use of FCS and related methods have increased dramatically in the last 10 years in academia and among biotechnological and pharmaceutical companies for studies of molecular interactions (see M. Auer, *Drug Disc. Today,* 1998, 3: 457, C Eggeling, L Brand, D Ullmann and S Jäger, *Drug Disc. Today,* 1998, 2003 8(14): 632). FCS is based on the analysis of intensity fluctuations of fluorescent molecules excited by a focused laser beam. The technique can in principle offer information about any molecular dynamic process in the nanosecond time range and longer that manifests itself as a change in fluorescence intensity. The fluorescence fluctuations are analysed in terms of the auto-covariance of the detected fluorescence intensity, normalised by the time-averaged fluorescence intensity squared.

$$G(\tau) = \frac{<F(t)F(t+\tau)>}{<F>^2} = \frac{<\delta F(0)\delta F(\tau)>}{<F>^2} + 1 \quad \text{(equation 1)}$$

For translational diffusion, the duration of the fluorescence fluctuations reflects the passage times of the molecules, while the relative amplitude of the fluctuations are inversely proportional to the mean number of molecules, N within the detection volume 102 (see FIG. 1). The correlation curve 202 reflects the probability versus time of detecting a fluorescence photon from a molecule, given that a photon was detected at time zero from that molecule (see FIG. 2). Consequently, the decay time of the FCS curve, $\tau_D$, reflects the passage time. The amplitude is proportional to the relative fluorescence fluctuations and 1/N.

In fluorescent molecules, i.e. fluorophores, emission of a fluorescence photon typically takes place in the subsequent relaxation, $k_{21}$ 302, following excitation of the ground singlet state ($S_0$) to the first excited singlet state ($S_1$) 304. The rate of relaxation from $S_1$ to $S_0$ ($k_{21}$) is typically of the order $10^9$ s$^{-1}$. In addition, transition to more long-lived, non- or weakly fluorescent transient states can take place 306, hereafter referred to as the transient state, and among which we take the lowest triplet state as an example to explain the background and illustrate the principles of the invention. Among others, states generated by photo-induced charge transfer or isomerisation in particular belong in the category of such transient states. They can also be monitored by FCS in a principally similar way as the triplet state (see Widengren J, Dapprich J and Rigler R. *Chem Physics,* 216, 417-426, 1997 and Widengren J. Schwille P. *J Phys Chem A.* 104(27):6416-6428, 2000).

Figure 3:
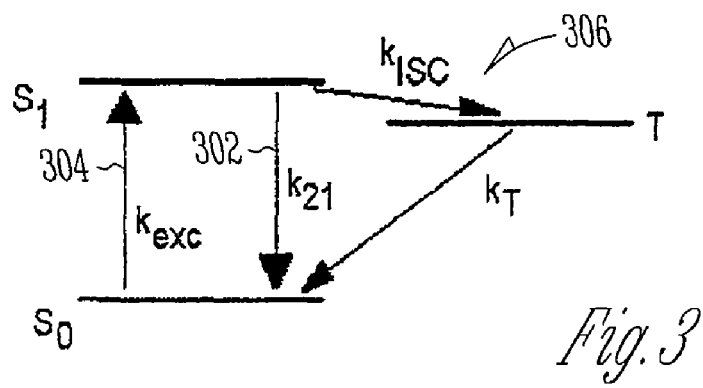

For the lowest triplet state (T), population takes place by intersystem crossing from $S_1$, typically with a rate ($k_{ISC}$) of the order $10^6$ s$^{-1}$ (see FIG. 3). The triplet state can be considered as totally non-fluorescent. From the ratio of the rate constants, $k_{ISC}/k_{21}$ it follows that transition to the triplet state takes place in approximately one per thousand of the excitation-emission cycles. However, once populated, the triplet state is quite long-lived (µs-ms). The triplet decay rate, $k_T$, is of the order $10^3$ to $10^6$ s$^{-1}$. As a consequence, the steady state population of triplet-state fluorophores accumulates strongly at high continuous excitation rates, i.e. when $k_{exc}$ is comparable to $k_{21}$ so that $S_1$ is significantly populated. Transitions to and from the triplet state generate fluorescence fluctuations, with the fluorophore being fluorescent while in the singlet entity ($S_0$ and $S_1$), but non-fluorescent while residing in the triplet state, T.

In FCS, these fluctuations are superimposed on those due to translational diffusion of the fluorescent molecules into and out of the detection volume 102 (see FIG. 1), and generate a second relaxation process in the correlation curves. In these correlation curves 402, the relative amplitude of this second relaxation process corresponds to the average triplet state population, $\overline{T}$, of the fluorophores in the detection volume. The relaxation time, $\tau_T$, corresponds to the relaxation time of the singlet-triplet transitions (see FIG. 4) (see J Widengren, Ü Mets, R Rigler, *J Phys Chem* 1995, 99, p. 13368). Following from FIG. 3, both these parameters depend on the excitation rate, $k_{12}$.

$$\overline{T} = \frac{k_{12}k_{23}}{k_{21}k_{31} + k_{12}(k_{23} + k_{31})} \quad \text{(equation 2)}$$

$$\tau_T = \frac{1}{k_{31} + k_{23}k_{12}/(k_{12} + k_{21})} \quad \text{(equation 3)}$$

Generating FCS curves at different excitation intensities, and determining $\overline{T}$ and $\tau_T$, makes it possible to determine all the rate parameters involved in the singlet-triplet transitions. FCS offers several important advantages to flash photolysis or transient absorption techniques for investigations of triplet states. In contrast to these techniques, FCS takes advantage of the inherent thermodynamic fluctuations to follow a kinetic process, without the need of any external synchronisation in the form of a perturbation. Triplet parameters derived from FCS are also well reproducible. In contrast, the reported triplet state rate parameters obtained by transient absorption techniques vary substantially between different reports.

Nonetheless, there are difficulties and disadvantages when using FCS. Although the method is relatively simple and powerful, triplet state monitoring by FCS is also afflicted with certain limitations. One of those is that low molecular numbers have to be recorded in order see the necessary spontaneous fluctuations. Therefore only low sample concentrations (<100 nM) can be monitored. Secondly, highly sensitive detectors with low noise levels are required and the time scale of the triplet fluctuations requires detection and processing of the fluorescence data with high time resolution. Only point detectors can meet these demands on the detection.

Probing the triplet state properties can yield useful molecular information. One use is to probe extent of triplet state induction or quenching. As for fluorescence quenching, these effects are primarily based on collisional interactions between fluorophores and molecules that can induce enhanced transition rates between different states of the fluorophores. In fluorescence quenching an additional non-fluorescent relaxation pathway from $S_1$ to $S_0$ is induced, thereby reducing the fluorescence. The decrease in fluorescence (or the decrease in the fluorescence lifetime of the fluorophore) can then be used to measure the degree of collisional interaction, which for instance can give information on the accessibility of the site of labelling, and how well shielded it is from the surrounding solvent (see FIGS. 5 and 6). The accessibility may change as a consequence of a conformational change or a molecular interaction, and can thus be used to monitor these Triplet states, on the other hand, are relatively long-lived (ms-μs) compared to $S_1$ (ns). Surrounding molecules that can affect the rate of triplet state deactivation, $k_T$, therefore have at least 1000 times as long time to collisionally interact with the triplet state. They can also induce an increased rate of intersystem crossing to T. Triplet state quenching/induction, monitored via triplet state kinetics, can thus give very sensitive information of the immediate environment of the fluorophores, reflecting for example molecular interactions or changes in protein conformations.

Apart from addition of molecules affecting formation or decay of triplet state fluorescent molecules, transitions to and from triplet states can be modified by excitation of $S_1$ and/or T to higher singlet or triplet states. For these higher states, the transition rates between the singlet and triplet entities of the fluorophores are different from those between $S_1/S_0$ and T, thereby altering the fraction of fluorophores being in a triplet state. Excitation to higher excited states (by a subsequent radiation field) can be performed at the same time as the excitation responsible for $k_{12}$, taking $S_0$ to $S_1$ (the $k_{12}$-excitation), and the optimal excitation wavelength is typically slightly red-shifted compared to that of the $k_{12}$-excitation. For an example of light-induced triplet quenching/modification by application of an additional excitation field (e.g. a field from an acousto-optical modulator, AOM 1402 in FIG. 14A), generated and monitored in an FCS experiment, see J. Widengren, C. Seidel, *Phys Chem Chem Phys*, 2000, 2: p. 3435-3441.

The subsequent radiation field can also be applied with some delay in time with respect to the $k_{12}$-excitation. Moreover, the radiation field can in addition to generating the subsequent excitation to higher excited states also be used to induce stimulated emission from an excited state to a lower state. By adjusting the delay in time between the $k_{12}$-excitation and the subsequent radiation field (hereafter referred to as $t_{delay}$) different stages of relaxation following the $k_{12}$-excitation can be specifically manipulated and interrogated by the subsequent radiation field. Following $k_{12}$-excitation, relaxation takes place, by vibrational relaxation within the electronic state of $S_1$ (typically ps range), by electronic relaxation of $S_1$ to $S_0$ (typically ns range), and by relaxation into more long-lived transient states (typically μs range and longer). Following $k_{12}$-excitation, the extent of vibrational relaxation at the time the subsequent radiation field is applied (at $t_{delay}$) influences the energy differences between $S_1$ and its neighbouring states, and thereby the spectral dependence for excitation or stimulated emission taking place from $S_1$ by the subsequent radiation field. On a longer time scale (typically ns), the extent of electronic relaxation at $t_{delay}$ determines the fraction of fluorescent molecules that still are in $S_1$ that can be excited to higher excited states or that can be subject to stimulated emission to a lower state. Similarly, at yet longer time scales, the extent relaxation to long-lived transient states has taken place at $t_{delay}$ determines what transitions that can be generated by the subsequent radiation field, simply by the distribution of states being present at a certain $t_{delay}$ after onset of the excitation radiation field (e.g. 1406 in FIG. 14A), determining the possible "starting points" for possible transitions influenced by this subsequent radiation field.

Fluorescence quenching experiments normally measures the extent of excited state depopulation as a consequence of fluorophore-quencher interaction. Since the fluorescence lifetime typically is in the nanosecond time range, the time available for interaction is about 1000 times shorter than for long-lived states, like triplet states. Procedures for triplet state quenching measurements has indeed also been implemented. However, a problem then is the monitoring of the triplet state population. It is usually monitored via transient triplet state absorption or via phosphorescence, generated by decay of the triplet state to the ground singlet state, but this is normally technically complicated to do and insensitive.

The FCS approach for triplet state monitoring relies on a strong excitation of the fluorescent molecules, such that the response in fluorescence intensity per molecule to the excitation intensity (or irradiance, in W/cm$^2$) is no longer linear in the excitation intensity range used, i.e. that the mean probability of populating the excited singlet state $S_1$ is no longer proportional to the excitation intensity. In FCS measurements high enough excitation intensities can easily be reached due to a strong focussing of the excitation laser beam (e.g. 1406 in FIG. 14A) under the microscope objective, where the molecules to be investigated are located. In fact, focussing the laser beam at or close to the limit of diffraction, with a beam waist radius in the focus of approximately 0.3 μm, excitation powers of less than 1 mW are sufficient to yield prominent triplet state populations in the fluorophores within the laser beam focal volume. Moreover, due to the small size of the focus, freely moving molecules typically pass the laser beam focal volume within times short enough to avoid photobleaching. Alternatively, given a laser focus for excitation, the passage times of the molecules, i.e. the exposure time to the excitation laser (e.g. 1406 in FIG. 14A), can be made shorter by applying either a scan or flow of the sample (with a stationary beam), or scan the beam (with a stationary sample).

Apart from molecular monitoring via triplet state quenching/induction (as outlined above), triplet state parameters can be exploited as a readout for intra- and intermolecular distances via so-called Fluorescence (Förster) Resonance Energy Transfer (FRET) FRET is a photo-physical process, and a well established tool to yield molecular distance information in the range of 10-100 Å (see T Förster, *Ann. Phys.* 1948, 2: p 55; L Stryer, R P Haugland, *Proc. Natl. Acad. Sci*, 1967, 58: p. 719) Via FRET, energy is transferred non-radiatively by resonance from a donor molecule to an acceptor molecule via an induced dipole-induced dipole interaction. The efficiency, E, with which transfer of excitation energy takes place depends on several parameters, such as the mutual orientation of the dipole moments of the fluorophores, the spectral overlap etc.

However, the usefulness of FRET relies primarily on the fact that E depends on the inverse-sixth-power of the distance, $R_{DA}$, between the donor and acceptor dye molecules, FRET thus provides what is referred to as a "molecular ruler". In traditional fluorescence spectroscopy, the FRET efficiency E can be monitored via several parameters, most commonly via the intensities of the donor and acceptor fluorophores (donor fluorescence decreases and acceptor fluorescence increases with higher E), or the lifetime of the donor (higher E leads to shorter donor fluorescence lifetimes). FRET has found a wide range of applications in the biomedical field. By use of microscopic techniques it has been possible to apply FRET to many different microenvironments, with little or no interference of the system under study FRET has also found a wide application as a basis for molecular binding assays. A photophysical framework for fluorescence signals generated by FRET being sensitive to molecular conformation, association and separation is disclosed in the article by BE A, Jares-Erdman and T. M. Jovin, Nature Biotechnology, Vol. 21, No. 11, November 2003.

Irrespective via what parameters the FRET efficiency is read-out, also this method has certain disadvantages. In particular, it can be problematic to account for incomplete labelling of the molecules, such that the calculation of E is based on a collection of molecules, containing a substantial fraction of molecules not labelled with both donor and acceptor fluorophores. Cross-talk of fluorescence can also cause problems, such that fluorescence of the donor is erroneously partly detected in the detector for the acceptor fluorescence, and vice versa.

Probing of triplet state properties by the proposed method is also likely to be useful for High-Throughput Screening (HTS), where molecular interactions are investigated in a highly parallelised and fast manner. Often, bioactive molecules are only available in minute amounts, but need to be discriminated against, and checked in terms of their interaction with, a large number of compounds. Because of its high sensitivity (single-molecule detection), fast read-out, and high specificity (many parameters available), fluorescence spectroscopy has become a key technology in biotechnology for drug discovery and diagnostics. As an indication of the commercial importance, one can refer to the very strong interest from pharmaceutical companies from all over the world to use ultra-sensitive fluorescence techniques for high-throughput screening of new potential drugs. Many of the HTS assays developed, involves FRET (and its inherent problems).

SUMMARY OF THE INVENTION

The described methods and related apparatuses according to prior art technology all have their respective disadvantages. In addition to the mentioned disadvantages, none of the above described known methods and technologies provide an accurate and reliable method for obtaining time-resolved information with a parallel read-out of triplet states, as well as other information relating to the levels and rates by which transient photoinduced states of fluorophores are populated and depopulated.

It is therefore an object of the present invention to provide a solution to the aforementioned shortcomings and problems as well as a new method for obtaining time-resolved information, not restricted to read-out from one or a limited number of small excitation spots/volumes. This is accomplished by means of a method and apparatus according to the independent claims.

Further advantageous embodiments of the present invention are set out in the appended claims.

The proposed solutions make it possible to interrogate long-lived, transient, photo-induced states in a highly parallelised, high-throughput manner with high sensitivity. The possibility to record the kinetic parameters of these states in this way, with the inherent exclusion of many artifacts typically encountered in fluorescence recording, combined with the sensitivity of these states for molecular interactions, which follows from the long lifetime of the states, render the present invention a very high precision and accuracy.

As compared with the known methods based on fluorescence quenching experiments, the present invention, utilising the approach of combining the quenching sensitivity of the triplet state with the sensitivity and specificity following from the use of fluorescence as a read-out mean, combines the advantages and circumvents the disadvantages of the separate use of either singlet-state or triplet-state quenching measurements. This is also true for the FCS approach. Similarly, the same principal advantage can also be exploited when monitoring quenching/induction of other categories of long-lived photo-induced transient non- or weakly fluorescent states. FCS has been demonstrated to be well capable of monitoring changes in populations of transient states generated by photo-induced charge transfer (see Widengren J, Dapprich J and Rigler R. Chem Physics, 216, 417-426, 1997) or isomerisation (see Widengren J. Schwille P. J Phys Chem A. 104(27): 6416-6428, 2000) due to addition of compounds promoting or suppressing the transfer rates to and from the particular state in question. The effect of the added compound can be induced via collisional interactions, or via changes in viscosity and polarity in the immediate environment of the fluorescent molecules or probes. However, in contrast to the FCS approach for transient state monitoring, the present invention allows for transient state quenching/induction experiments to be performed on a massive parallel scale opening also for high throughput screening applications. Further, it is not limited to the monitoring of molecular concentrations lower than ~1 µM.

Quenching/induction of transient states can also be introduced by one or several subsequent radiation fields. The distribution of states being present at a certain time $t_{delay}$ after onset of the excitation radiation field (e.g. 1406 in FIG. 14A), or after cessation of the excitation field pulse, determines the possible "starting points" for possible transitions influenced by this subsequent radiation field. In this way, a three-state kinetic scheme such as that shown in FIG. 3, with the population of the states being controlled by the $k_{12}$-excitation, can be extended with additional states, where one or several of the transitions between the states can be influenced by light, and where thus the population kinetics are determined and possibly modulated by the characteristics of the additional radiation field(s), in particular by its intensity, duration, and possible $t_{delay}$, but also its polarization, and shape in time and space.

Figure 14A:
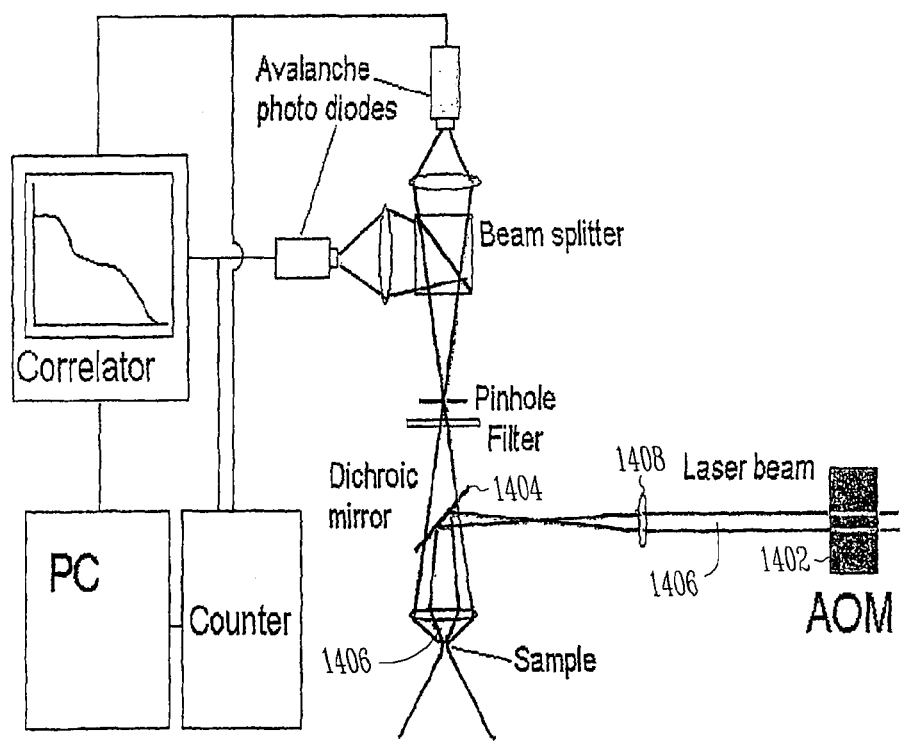

Likewise, beating patterns can be generated if the resulting fluorescence is a product of the excitation field (e.g. 1406 in FIG. 14A) and one or several of the additional radiation fields (such as a field entered via the AOM 1402 in FIG. 14A). With spatial or temporal modulation of these fields, spatial and temporal beating patterns can appear, with frequencies given by the differences of the excitation and additional radiation fields, but also influenced by the transient state kinetics.

Changes in the transient state kinetics can possibly generate large relative changes in the beating frequencies, which thus may serve as a possible readout of the transient state parameters.

FCS should likewise be applicable to the monitoring of transient state kinetics also under these kinds of conditions, applying additional radiation field(s), and using this latter category of state model. However, the transient state monitoring concept described by the invention enables parallel monitoring with much less constraint in molecular concentrations.

A possible extension to this light-induced modification of the kinetics of the transient state(s) by at least one subsequent radiation field is to introduce a feed-back, in which the response on the transient state parameters can be used to guide the adaptation of the pulse characteristics. One purpose would be to facilitate the adaptation of the pulse characteristics such that minor changes in transient state rate parameters (due to molecular interactions or microenvironmental changes around the fluorescent molecules) generate maximal effects on the transient state parameters monitored. The extent and modality (in particular excitation intensity, pulse duration, shape in time and space, $t_{delay}$, polarization) of adaptation of the pulse characteristics needed to generate a certain (clamped) set of transient state parameters can then also be used as a read-out. This principle of active feed-back to improve read-out contrast, and the use of the feed-back needed to clamp the parameters as a read-out by itself is similar to concepts practiced for instance in atomic force microscopy, e.g. force-clamped tapping mode AFM (Jalili and Laxminarayana, *Mechatronics* 14 (2004) p. 907-945), and so called active-Q feed-back (Hörber and Miles, *Science* (2003), p. 1002-1005), respectively.

The invention thus open up for monitoring of any molecular interaction that is reflected as a change in photo-induced transient states, such as triplet states, and states induced by photo-induced isomerisation, electron transfer, or FRET. As a few examples can be mentioned:

Use as a read-out concept for DNA- and protein arrays. Hybridisation/molecular interactions can be monitored in a highly parallel fashion, both using a solid-support array, or an array of wells containing solution. In this setting, the proposed approaches open for the use of a new, powerful, yet unexploited set of sensitive and significant fluorescence-based parameters for HTS applications.

The invention can provide novel transient state parameters in addition to the "traditional" fluorescence parameters (intensity, wavelength of excitation and emission, fluorescence lifetime, and polarisation). The increased number of independent parameters can offer an enhanced possibility of identifying and proving the presence of disease-specific molecules, or molecular interactions, within for instance an array of samples.

In the field of imaging of environmental factors, fluorophores, either free or conjugated to other molecules, can via their triplet states (or charge transfer states) reflect the concentrations of quenchers, for instance of molecular oxygen. Likewise, trans-cis isomerisation properties can probe local viscosities and forces (for instance as an effect of microenvironment or molecular interactions). The proposed approaches therefore offer a new method for micro environmental imaging, of arrays of samples (in micro wells or on solid support), as well as of surfaces and interiors of e.g. cells.

BRIEF DESCRIPTION OF THE DRAWING FIGURES

The above and further features, advantages and benefits of the present invention will be apparent upon consideration of the following detailed description, in conjunction with the accompanying drawings, in which reference characters and figures refer to like parts throughout, and in which:

FIG. 1 illustrates a schematic view of the detection volume in FCS, determined by the dimensions of focus of the laser beam 104 exciting the fluorescent molecules 106, and the collection efficiency function 108 of the microscope.

Figure 2:
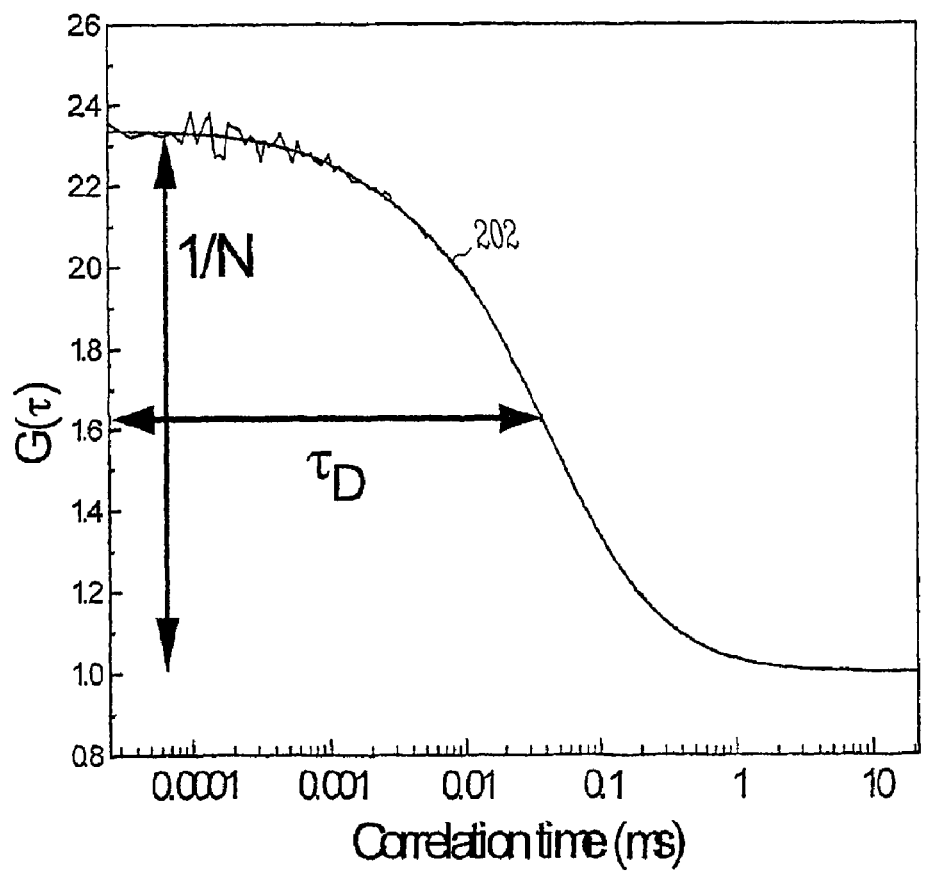

FIG. 2 depicts a characteristic recorded FCS curve 202 reflecting translational diffusion of the fluorescent molecules in the solution. The amplitude of the correlation curve scales with the relative fluctuations of the detected fluorescence intensity from the detection volume, and is proportional to 1/N, where N is the mean number of fluorescent molecules present in the detection volume. The decay time, $T_D$, of the FCS curve reflects the passage times of the fluorescent molecules through the detection volume.

FIG. 3 illustrates the traditional three state model for singlet-triplet transitions. $S_0$ and $S_1$ denote the ground and excited singlet state, respectively. T is the lowest triplet state. $k_{21}$ signifies the deactivation from $S_1$ to $S_0$ 302, $k_{ISC}$ is the rate of intersystem crossing from $S_1$ to T 306 $k_T$ is the triplet state deactivation rate to $S_0$, and $k_{exc}$ is the excitation rate 304, which is proportional to the applied excitation intensity $I_{exc}$.

Figure 4:
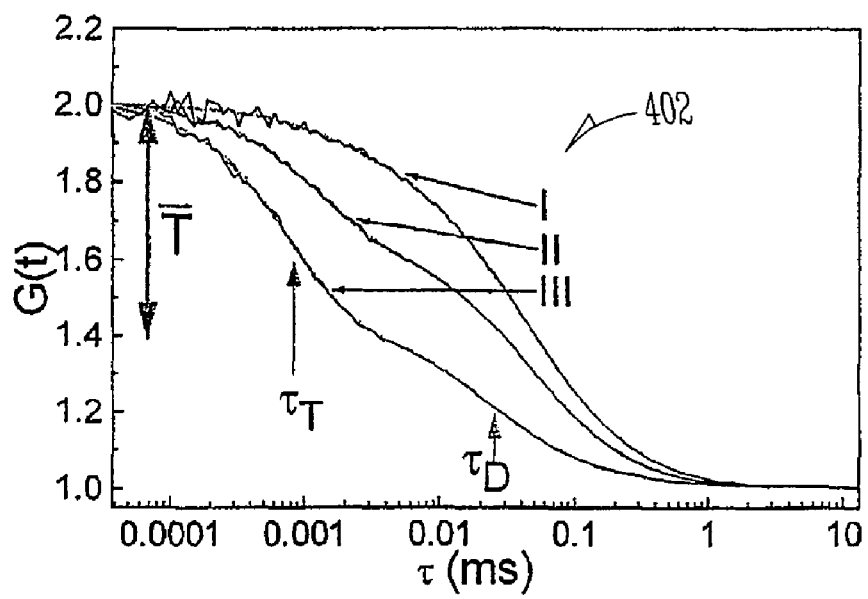
Figure 5:
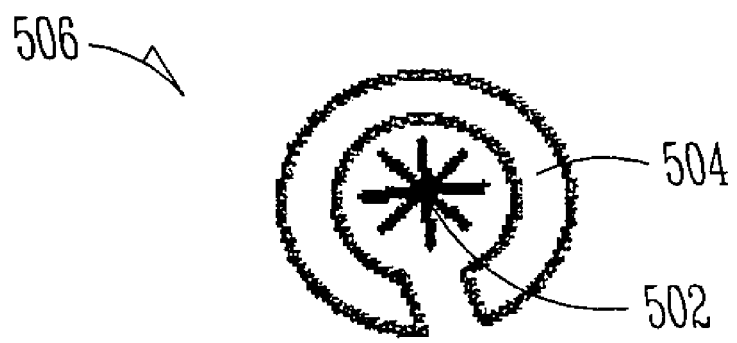
Figure 6:
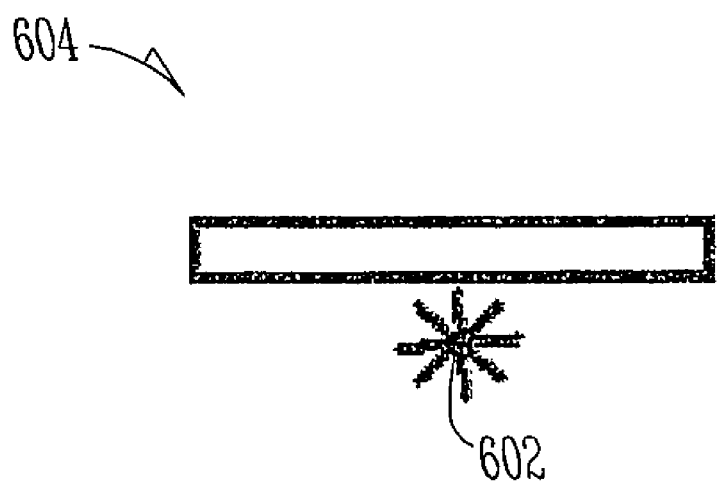

FIG. 4 depicts correlation curves 402 from molecules of the fluorophore Rh6G in water, undergoing translational diffusion and singlet-triplet transitions. Two relaxation processes can be identified, caused by translational diffusion (relaxation time $\tau_D$) and singlet-triplet transitions (with a relaxation time denoted $\tau_T$). The average triplet state population and triplet relaxation time are given by equations 2 and 3, and increases with higher excitation powers. I: 48.4 µW, II: 350 µW, III: 2.55 mW FIGS. 5 and 6 schematically illustrate fluorescence quenching as a measure of conformational state; where FIG. 5 illustrates a fluorophore 502 shielded 504 from a surrounding solvent with quenchers 506, thus fluorescent; and where FIG. 6 illustrates a fluorophore 602 unshielded, and thus its fluorescence is quenched (due to access of quencher molecules 604 to the fluorophore 602).

Figure 7:
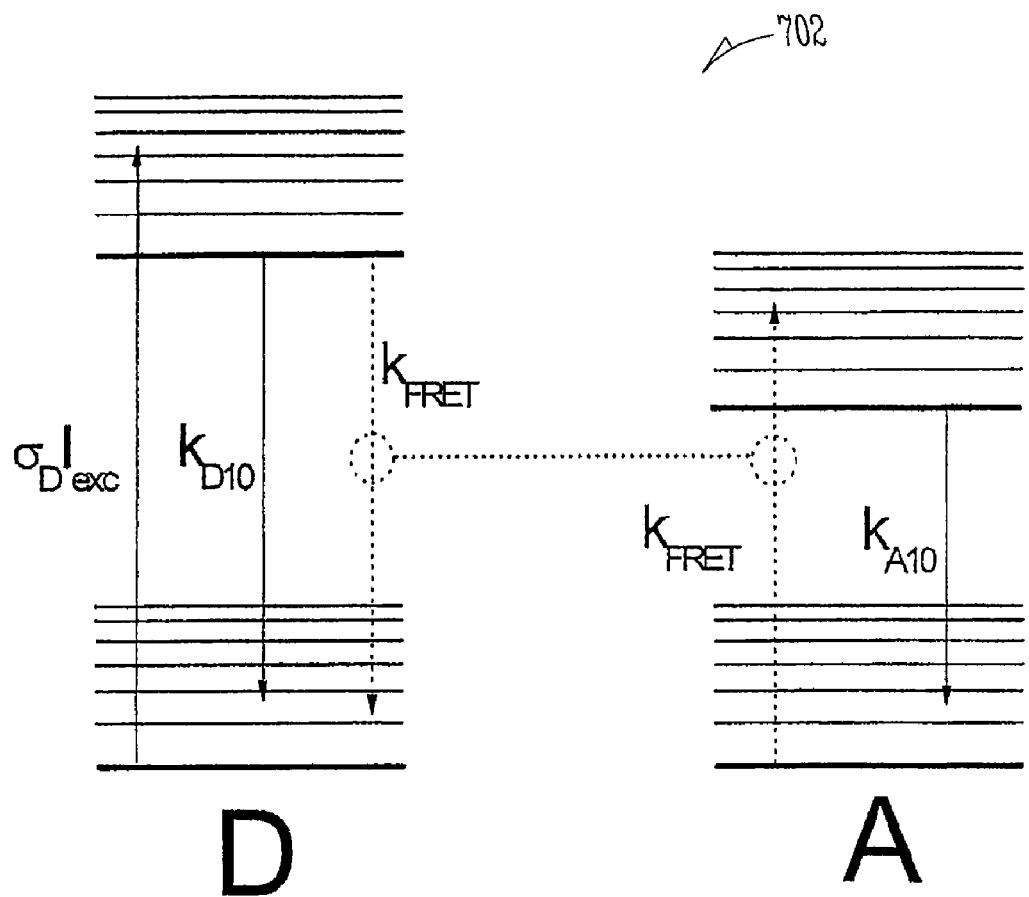
Figure 8:
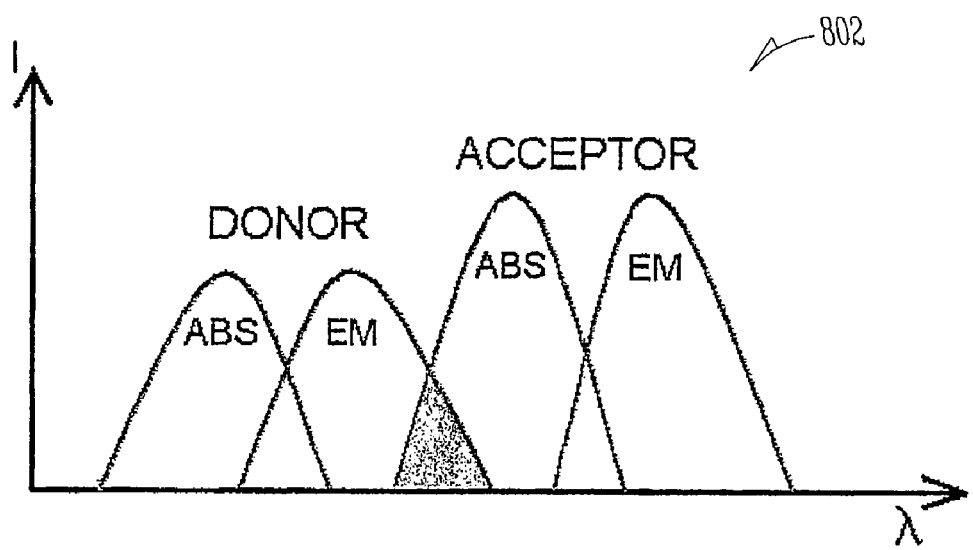

FIGS. 7 and 8 depict Fluorescence resonance Energy transfer (FRET) (702; 802)—transfer of excitation energy from a donor (D) to an acceptor (A) fluorophore in a strongly inter-fluorophore distance dependent manner. $\sigma_D$=excitation cross section of donor, $I_{exc}$=excitation intensity of donor, $k_{FRET}$=quenching rate of donor due to FRET, $k_{FRET}$' excitation rate of acceptor due to FRET, $k_{D10}$=intrinsic fluorescence decay rate of donor, $k_{410}$=intrinsic fluorescence decay rate of acceptor. Gray shaded area in FIG. 8 is the spectral overlap between donor emission and acceptor absorption.

Figure 9:
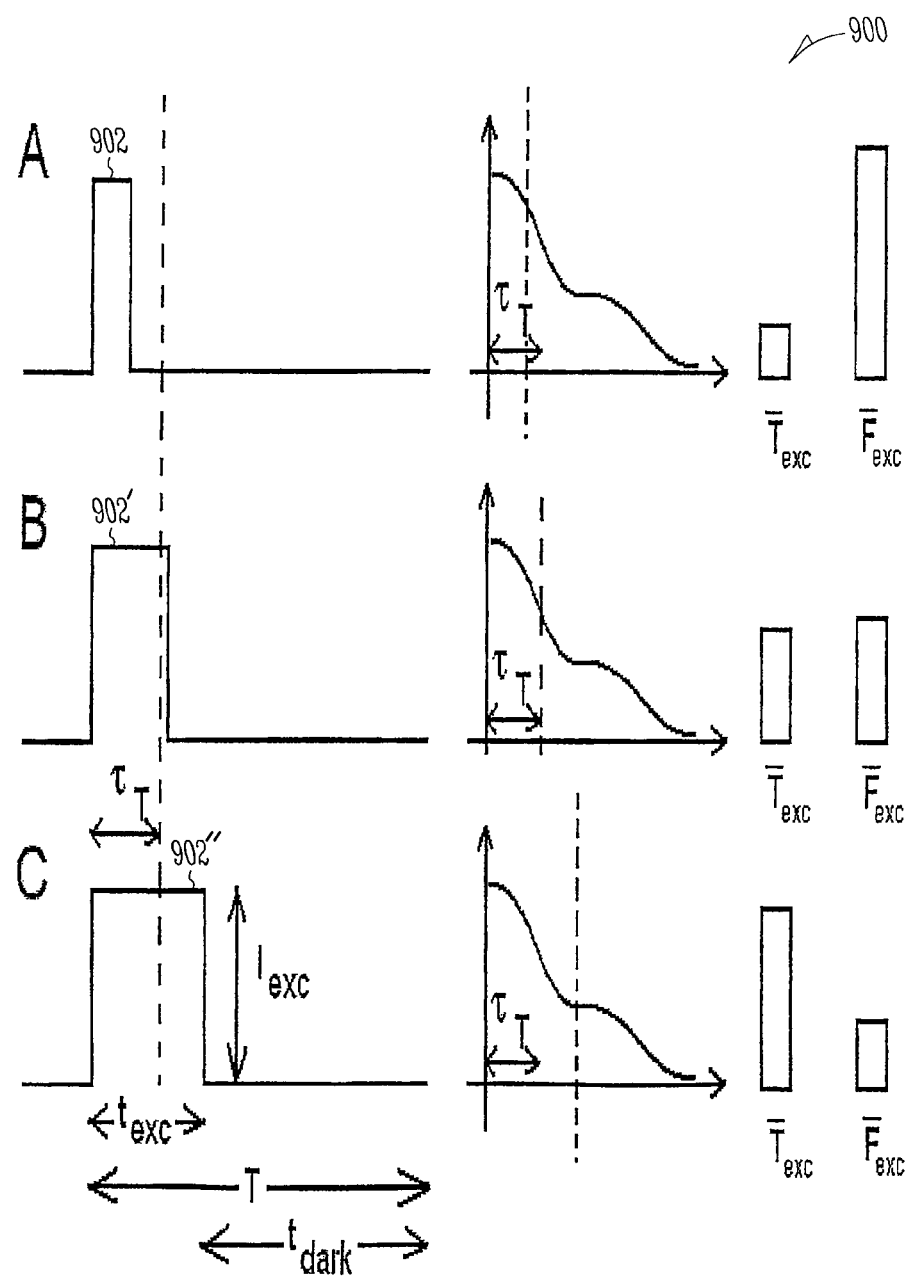

FIG. 9 illustrates the effect 900 of excitation pulse (902; 920'; 902") duration on the population of the triplet state. A fluorescent molecule that when subject to a continuous excitation $I_{exc}$ is populated in its triplet state with a probability of T and then having a singlet-triplet relaxation time of $\tau_T$ (eqs. 2 and 3) is considered.

A. Duration of the excitation pulse, $t_{exc}$, is much shorter than the triplet state relaxation time, $\tau_T$ (left). The fluorophore will be exposed to the excitation intensity for a too short time to significantly enter into the triplet state (middle). The mean triplet state population ($T_{exc}$) during the excitation period will be low, and the mean fluorescence intensity during the excitation pulse ($F_{exc}$) is relatively unaffected by triplet state accumulation (right).

B. $t_{exc}$ is similar to $\tau_T$, resulting in an increased triplet accumulation during the course of the excitation pulse (left and middle). $T_{exc}$ increases on expense of $F_{exc}$ (right).

C. For durations of the excitation pulse much longer than $\tau_T$ the fraction of fluorescent molecules in their triplet states will approach the level found during continuous excitation. While $T_{exc}$ is increased, approaching T, $F_{exc}$ is significantly lowered (right).

Consequently, comparing $F_{exc}$ (reflecting the fraction of fluorophores not in the triplet state, and proportional to $1-T_{exc}$) for different pulse durations, $t_{exc}$, makes it possible to determine the triplet state population during the excitation pulse, $T_{exc}$. The triplet state relaxation time can be determined from $t_{exc}$, by the way $F_{exc}$ increases with shorter $t_{esc}$. The duration between two consecutive pulses, $t_{dark}$, should typically be long enough that the triplet state population probability of the fluorescent molecules is negligible at the start of the next excitation pulse. However, also $t_{dark}$ can be varied such that comparison of $F_{exc}$ for different $t_{dark}$, reflecting extent of triplet state relaxation between pulses, can yield triplet state information (triplet state relaxation time and $T_{exc}$).

Figure 10:
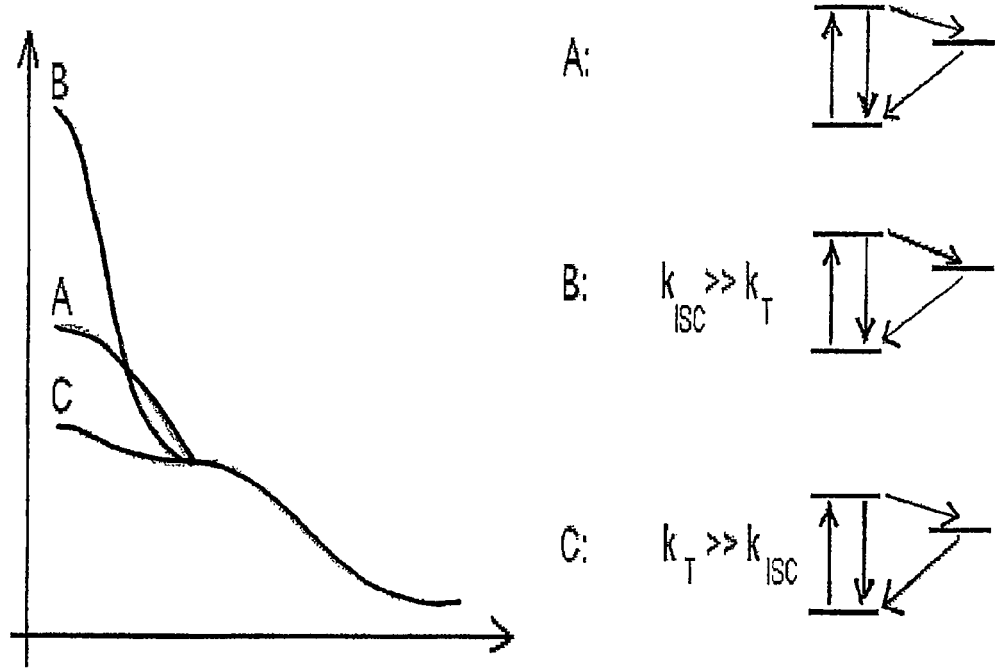

FIG. 10 illustrates differential quenching. Left: Triplet state populations as seen by FCS in three examples. A: No quencher, B: Dye1+quencher, C: Dye2+quencher. In the absence of quencher, two different dyes show a similar triplet state population at saturating excitation intensities (A). Depending on if $k_{ISC}$ or if $k_T$ is most influenced by the quencher, the triplet state population of the dyes will either increase (B) or decrease (C).

Figure 11:
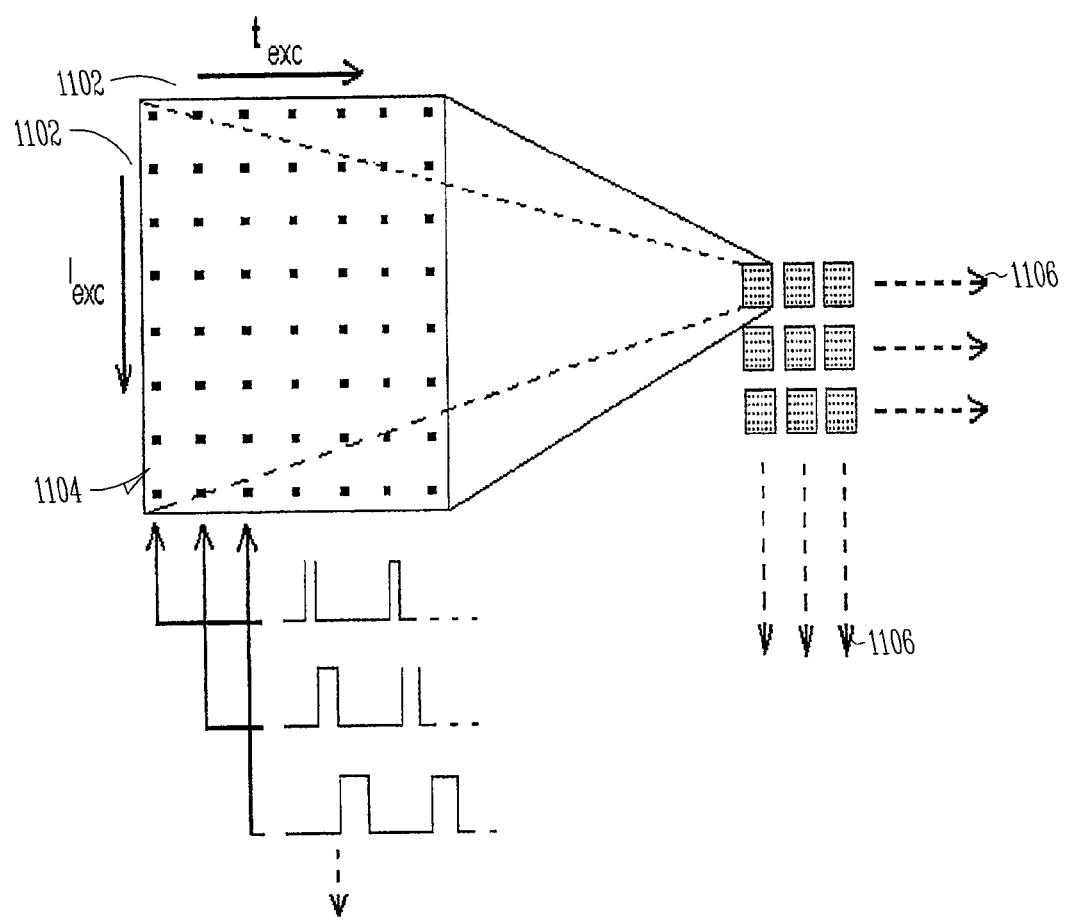

FIG. 11 discloses a possible realisation of the fourth embodiment of the present invention. Left: matrix of excitation regimes. Right: sample arrays, including variation of reagent and quencher concentrations. Matrices of excitation regimes 1102 are applied onto a sample area, which can be a small micro-well 1104 within a micro-well array plate 1106, or a spot (1104) within an array of spots (1106) of solid-supported DNAs or proteins. Wide-field excitation is used, which can be arranged as an array 1102 and 1106 of spots. Periodic excitation with spatial variation of $t_{exc}$ can be introduced by periodic deflection (such as within AOM (1402) or a deflection of a mirror (1404) in FIG. 14A) of the excitation field 1406, with the speed varying over the deflection cycle (such as within AOM 1402 in FIG. 14A), or by other means of spatially varying the modulation in time on different locations. The $L_{exc}$ gradient can be introduced by an attenuation filter (e.g. placed at 1408 in FIG. 14a; within the laser beam passing the AOM 1402 in FIG. 14A) with a spatial gradient. Multiple excitation arrays can be created by division of the original excitation beam (such as within AOM 1402 in FIG. 14A) by for instance multiple semi-transparent mirrors, by spatial light modulators, acousto-optic defectors, or by use of gratings or other types of diffractive optics.

Figure 12:
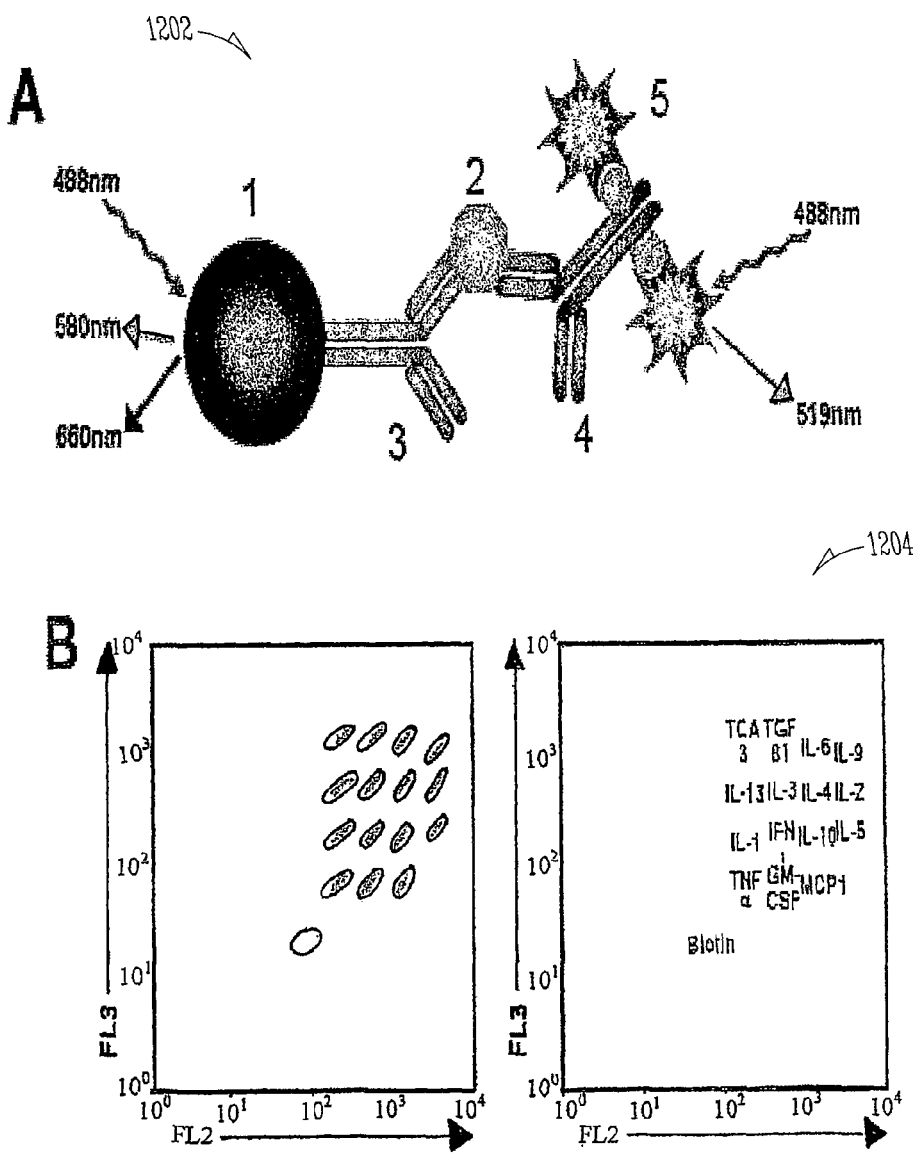

FIG. 12 illustrates the principle for fluorescence-coded microbead assays 1202. A: Principal arrangement of bead and antibodies 1: Polymer bead, 2: analyte, 3: capture antibody, 4: Biotinylated detection antibody, 5: Fluorophore coupled to streptavidin. B: Example of histogram of beads 1204, sorted with respect to their fluorescence intensity in two different wavelength ranges (FL1 and FL2). From the absolute levels of FL1 and FL2, the beads with different antibody coatings can be identified (B, right side).

Figure 13:
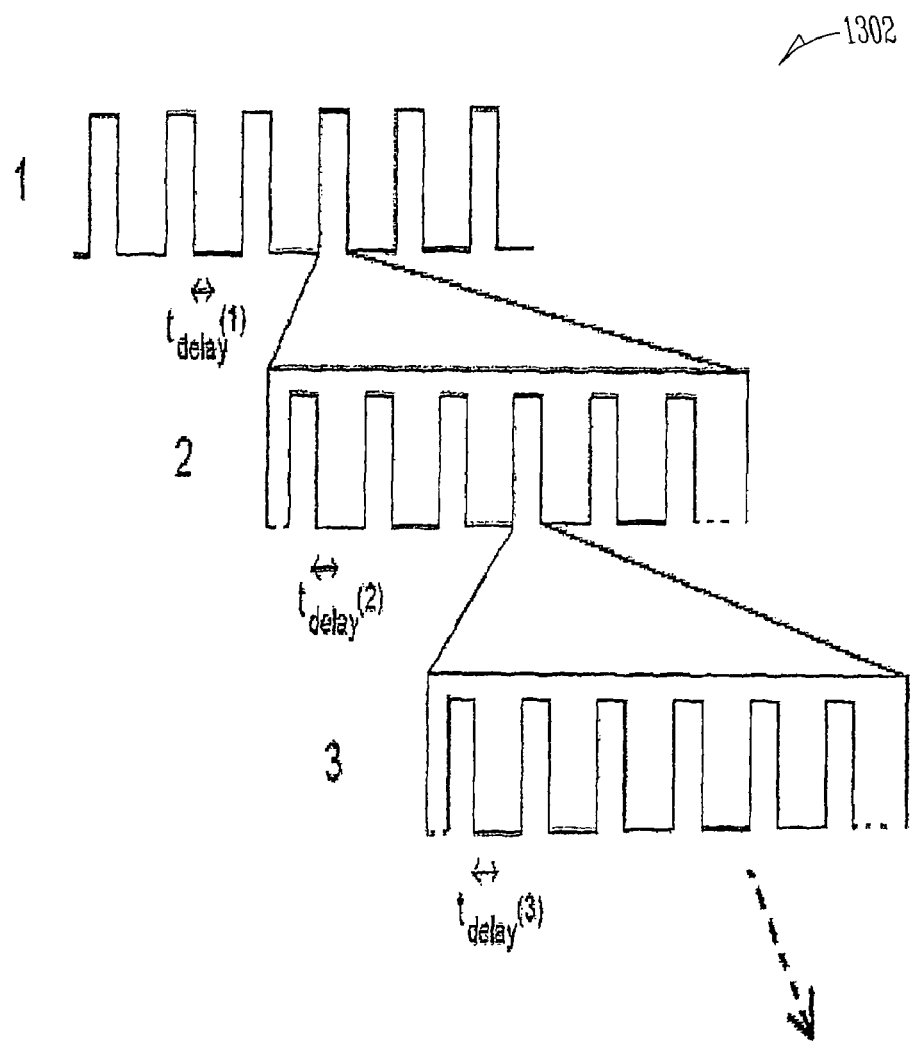

FIG. 13 illustrates a possible realization having several hierarchies 1302 of pulse trains within different time domains. A radiation field (e.g. 1406 in FIG. 14A) is modulated in time, generating a pulse train with certain pulse characteristics (line 1). On the pulse train of line 1 can in turn a modulation at a higher frequency be superimposed. The pulses of pulse train 1 can then contain additional pulse trains (line 2), with their specific pulse characteristics. If yet a higher modulation is introduced, a third hierarchy of pulse trains can be generated, and so on. Apart from the pulse characteristics of the pulses within each pulse train hierarchy, the pulses within a certain pulse train hierarchy can be delayed with respect to the pulses within the same pulse train hierarchy of another excitation or radiation field.

Figure 14B:
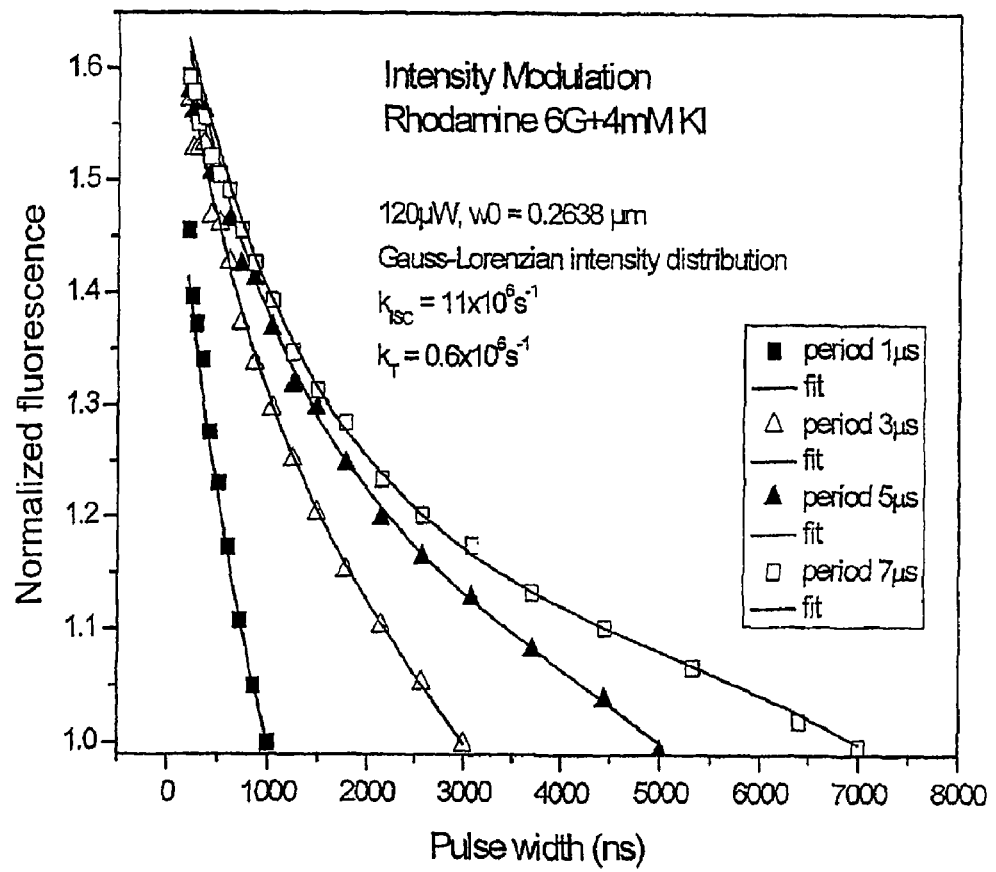

FIG. 14 shows a simple realization of the invention, in which the mean fluorescence intensity from Rhodamine 6G molecules in aqueous solution with potassium iodide is recorded from an epi-illuminated confocal detection volume element (FIG. 1) of a typical FCS instrument (FIG. 14A). The laser beam excitation is subject to modulation in time by an acousto-optic modulator (AOM) 1402 that generates rectangular excitation pulse trains. FIG. 14B shows the average fluorescence intensity under modulated excitation within the excitation pulses, with durations $t_{exc}$ and period times of $t_{exc}+t_{dark}$, normalised by the fluorescence intensity under continuous excitation. The triplet state parameters can be extracted from the variation of the fluorescence with $t_{exc}$ and the period time, and is in agreement with those extracted by time-resolved detection and correlation analysis by FCS in the same instrumentation.

DETAILED DESCRIPTION OF THE INVENTION

The following description is of the best mode presently contemplated for practicing the invention. The description is not to be taken in a limiting sense, but is made merely for the purpose of describing the general principles of the invention. Accordingly, we use the lowest triplet state of fluorescent molecules as an example of a transient state that can be monitored by the invention. The scope of the invention should be ascertained with reference to the appended claims.

In a first embodiment according to the present invention, control, manipulation, and monitoring of $T_{exc}$ is done by periodic excitation with different pulse durations and excitation intensities. As previously mentioned, an FCS curve reflects the probability of detecting a fluorescence photon from the molecule under investigation, given that a fluorescence photon was emitted from it at correlation time, $\tau=0$. Looking at FIG. 4, the fluorophore must be in the singlet entity at $\tau=0$ (since it then emitted a photon). The first relaxation process in the FCS curve reflects the transit of the fluorophore from the singlet entity ($S_0$ or $S_1$) into a steady state, where it has a probability of T to be in the triplet state (thus the lower amplitude=probability to emit a photon). In other words, at $\tau=0$, the probability to find the fluorophore in a singlet state (available for fluorescence) is $S_0+S_1=100\%$, and the fluorophore is fully fluorescent. At $\tau\gg\tau_T$ the fluorophore has relaxed into a steady state, with $S_0+S_1=1-T$, and with a corresponding reduction in its average fluorescence brightness (At $\tau_D$, the fluorophore is typically about to pass out from the detection volume, and the probability to detect a fluorescence photon from it approaches zero).

The FCS curve reflects the same probability function, with the same initial condition ($S_0+S_1=100\%$) as if a fluorescent molecule would experience the same constant excitation intensity, initiated at time t=0. Then, as for FIG. 4, the triplet population as a function of time after initiation of the excitation pulse, T(t), would be zero at t=0. T(t) would be negligible for t≪$\tau_T$, gradually increase with longer t, and finally approach a steady state population, T, for t≫$\tau_T$. Consequently, with different durations of the excitation period, $I_{exc}$, the average triplet population during the excitation period $T_{exc}$, will be different, and so will the mean detected fluorescence intensity, $F_{exc} \propto (1-T_{exc})$, which can be used to determine $T_{exc}$.

Using periodic excitation (constant excitation intensity, $I_{exc}$, during $t_{exc}$, followed by no excitation during time $t_{dark}$, with a total period time of $P_t=t_{exc}+t_{dark}$, see FIG. 9), and varying $I_{exc}$ and $t_{exc}$ for different pulse sequences, T(t) and the triplet state rate parameters $k_T$ and $k_{ISC}$ can be determined without the time-resolution on the detection side. The procedure can be as follows: The total fluorescence over time $F_{tot} \int F(t)dt$ at periodic excitation is recorded, with the duration of excitation, $t_{exc}$, varying from one recording to the next. A period time, $P_t$, is used, which is long enough that the triplet states relax back during $t_{dark}$. By recording $F_{tot}$ at different $t_{exc}$, $t_{dark}$ and $I_{exc}$, the triplet state properties can be fully characterised, as for FCS, but without the restraints of point detection, low concentrations, or detection with high time resolution and sensitivity. Following this principal approach, differences in $F_{tot}$ can be generated by variation of excitation pulse characteristics more generally, including in addition to variation of $t_{exc}$, $t_{dark}$ and $I_{exc}$ also variations in pulse shape in time and space, and polarization, and can subsequently be used to monitor a range of photo-induced transient states.

Likewise, applying at least one additional radiation pulse field (such as a field entered through AOM 1402 in FIG. 14A), additional manipulation(s) and modulation(s) of the population kinetics of transient states are possible, by varying the same said pulse characteristics for the additional radiation field(s), and in addition also by possible variation(s) of shifts in wavelengths, phases and modulation frequencies of the additional radiation fields in relation to the excitation field. The pulse sequences of the excitation field and the additional radiation field(s) can contain at least one additional hierarchy of pulse trains on a faster time scale, superimposed on the original pulse train. Each hierarchy of pulse trains can have their specific pulse characteristics, and each of them can possibly be shifted in time by a specific $t_{delay}$ with respect to the pulses of the corresponding hierarchy of pulse trains of the excitation field, or to the pulses of the other possible additional radiation field(s) at the same hierarchy level. In this way, several different stages of the relaxation following $k_{12}$-excitation can be specifically manipulated and interrogated at the same time, via $F_{exc}$ at each hierarchy level, and eventually via the recorded $F_{tot}$.

This available application of additional radiation fields makes it possible to manipulate/modulate the transient state kinetics, and enhance contrasts in the transient state kinetic behaviour as a response to a molecular event or interaction. Addition of a feed-back control from the transient state kinetic behaviour back onto the pulse characteristics of the excitation field and possibly also the subsequent radiation field(s) can serve as a means to optimize this contrast enhancement. Moreover, by use of clamping of the transient state kinetics by active feed-back, the extent and modality of feed-back can be used as the actual read-out.

Since the triplet state is much more long-lived than $S_1$ (and therefore has a much longer time under which it can be influenced by collisions and by other interactions with the direct environment of the fluorophore), it typically can provide a much more sensitive readout for quenching than what $S_1$ quenching can do. Apart from previous problems with triplet state monitoring, which can be overcome by applying a solution according to the mentioned first embodiment, triplet state quenching/induction can also be difficult to use because of unspecific interactions between the fluorophore and its surrounding influencing the triplet state.

In accordance with a second embodiment of the present invention, a solution for how to more reliably probe the extent of triplet state quenching is proposed (see FIG. 10). The triplet state population can be strongly enhanced by addition of quenchers, which by the so called heavy-atom effect enhance the rate of intersystem crossing, $k_{ISC}$. This can be very clearly seen in FCS measurements as a prominent increase in the triplet population. However, we have observed that for some fluorophore/quencher combinations, the triplet decay rate, $k_T$, is far more enhanced than the intersystem crossing. Depending on if $k_{ISC}$ or $k_T$ is most strongly increased, the triplet population will either markedly increase or decrease upon addition of a quencher, if the excitation intensity is high enough to produce a steady-state triplet population in the first place (see FIG. 10). This is hereafter referred to as differential quenching. Consequently, using two different fluorophores emitting in different wavelength regions, and that react differently on the addition of a triplet state quencher/inducer, its influence can be monitored in a highly significant way as an increase in fluorescence intensity and decrease in triplet state population for one fluorophore, and a concomitant/coupled decrease in fluorescence intensity/increase in triplet state population for the other fluorophore.

In accordance with a third embodiment of the present invention, FRET is proposed in combination with application of differential quenching. As can be seen in equations 2 and 3 above, both T and $\tau_T$ depend on the excitation rate $k_{12}$. This dependence remains, no matter the mode of excitation Consequently, if the excitation takes place via FRET, the triplet state parameters of the acceptor can be used to determine the rate of FRET-mediated excitation from the donor, and hence the FRET efficiency E. While the triplet state population of the acceptor should preferentially be prominent, in order to clearly see also smaller changes in E, the triplet population of the donor should be low to minimize interference in the transfer of excitation energy to the acceptor. The proposed solution is to use differential quenching, where the triplet population of the donor is decreased, while that of the acceptor is increased.

When applying the combination of FRET and differential quenching, the following advantages can be expected:

Very small effects from donor fluorescence cross-talk and background (although there is some cross talk of donor fluorescence, or background leaking into the acceptor channel, they will not show the characteristic relaxation time of the triplet-influenced acceptor fluorescence)

Minimised effects from incomplete labelling (since the FRET efficiency is read via the acceptor fluorescence, practically only those molecules having both donor and acceptor fluorophores labelled to them will show a signal).

Calibration of concentrations, absolute fluorescence, or detection quantum yields is no longer required (the triplet parameters are extracted only from parameters that are related to the acceptor fluorescence itself. Calibration of the triplet parameters themselves can be done by direct excitation of the acceptor with known excitation intensities, i.e. no additional molecules are necessary for the calibration).

In accordance with a fourth embodiment of the present invention is utilised the readout of $T_{exc}$, reflecting T and $\tau_T$, which in turn reflect induction/quenching and FRET (according to the previously discussed second and third embodiments) by use of the first embodiment in a parallel way, for higher accuracy, precision and throughput.

It is highly interesting to be able to parallelise the triplet state monitoring for higher throughput analyses. Triplet state monitoring by FCS would be extremely difficult and expensive to realise on a massive parallel scale for high-throughput purposes. It would require construction of a matrix of detectors individually and accurately aligned with respect to, and registering fluorescence from, a corresponding matrix of laser foci.

In contrast, the first embodiment can be realised in a highly parallel fashion for HTS by use of a matrix of laser foci, or other patterned or even uniform wide-field excitation and matrix detection by one CCD camera (with approximately 1000×1000 dot detection), the detection and/or excitation possibly combined with optical spatial filtering/sectioning, Optical spatial filtering/sectioning on the detection side has the purpose to spatially confine fluorescence detection to areas/volumes in which the excitation conditions are well defined. This can be performed by, but is not limited to, means including an array of pinholes in the image plane, or masks in the image plane that can be changed spatially and/or temporarily, such as a Nipkow disc. Filtering/sectioning can also be performed on the excitation side by use of two-photon excitation, evanescent field excitation by total-internal reflection, or by various ways of patterning/masking of the excitation field spatially and/or temporally. The excitation regimes can be varied in terms of the pulse duration, $t_{exc}$, durations of dark time intervals between excitation pulses, $t_{dark}$, and the excitation intensity of the pulses, $I_{exc}$, but also by the polarization and shape of the pulses in time and space, over the spatial dimensions of detection. Each excitation regime array can then make up positions in an additional hierarchy of arrays, based on different concentrations of quenchers, spectral separation of the fluorescence emission by prisms, gratings, or mirrors, or on sample arrays.

In this way, the concept unites high accuracy and precision, with high sensitivity—the detection quantum yield of a CCD camera can be as high as for an avalanche photodiode, used in FCS- and through-put. Molecules and molecular interactions taking place on single molecule level to high concentrations (mM-M) can be monitored. As an alternative to excitation regime arrays, within which $t_{exc}$, $t_{dark}$, $I_{exc}$ and other pulse characteristics are varied over a spatial scale in the sample, a corresponding variation of the pulse characteristics can also be executed in one and the same sample location by application of sequential pulse trains with different pulse characteristics.

The presented concepts can be extended to other photo-induced processes than singlet-triplet transitions, for which an initial condition for the population of the different states can be defined at the start of the excitation pulse (corresponding to $S_1+S_0=1$ in the triplet state example). By FCS we have analysed several other photo-induced processes, that like triplet state transitions show similar relaxation kinetics, and for which the same kind of initial condition (population of the photo-induced state is zero at $\tau=0$, or $t_{exc}=0$) applies Photo-induced electron transfer and trans-cis isomerisation within cyanine-type fluorophores belong to such processes.

Photo-induced electron transfer has been observed by FCS for several dyes interacting with certain nucleotides, in particular dGTP. It can be seen as a prominent relaxation process preceding that of triplet state relaxation. Concept I can then be applied in a similar fashion as for triplet state kinetics. The strong variation between different nucleotides, and the strong distance-dependence of the interaction, would make it possible to follow sequence-specific hybridisation of fluorophore-labelled primers to target-DNAs of interest, as in DNA arrays.

As for triplet state monitoring, concept I is also applicable for isomerisation characterization. Trans-cis isomerisation within cyanine fluorophores is a photo-induced twisting of the hydrocarbon chain connecting the two head groups of the fluorophores. The twisting is faster in the absence of steric hindrance, and at low viscosities. The isomerisation kinetics can also be influenced by molecular forces or strains acting onto the fluorophore. A molecular interaction can thus easily affect these parameters, and is then reflected by, and can be monitored via, a change in the isomerisation kinetics.

As an alternative to microarrays, bead-based assays combined with fluorescence-activated cell sorting (FACS) have been developed to perform multiplexed molecular assays. The first embodiment when applicable in combination with the second embodiment can also be used in this context.

In multiplexed bead-based assay systems the different capture molecules are coupled to specifically-coded polystyrene microspheres, typically 5-6 μm in diameter. The individual microsphere is colour-coded by a distinct mixture of fluorophores at different doping concentrations, and with different emission spectra.

Binding of analyte molecules to their respective capture molecules can be monitored in a sandwich-assay, with fluorescent anti-bodies binding to a second epitope, emitting in an additional separate spectrum (see FIG. 12). The signal intensities of the individual beads are measured in a FACS apparatus. From the fluorescence code of the beads (the so called fluorescence bar code) it is possible to identify to which molecules the analyte has bound (see FIG. 12 B), and from the fluorescence of the second antibodies to quantify the degree of binding (see FIG. 12 C). In FIG. 12 B the beads are loaded with two fluorophores in four different distinct concentrations, providing 16 different fluorescence codes, Colour-coded microspheres can be used to perform up to 100 different assay types simultaneously (Lab P system, www.luminexcorp.com).

A limitation in the number of differently coded beads that can be used simultaneously is given by the spectral emission overlap between the different fluorophores loaded into the beads (in FIG. 12 there are just two different fluorophores).

Using the first embodiment, exciting the beads in at least two different modes while they are flowed through the FACS apparatus, where at least one characteristic parameter of the pulse train ($t_{exc}$, $t_{dark}$, $I_{exc}$, polarisation, and pulse shape in time and space) is different between the modes, the extent of triplet population can be determined from the difference in the fluorescence intensity generated in the different modes (see FIG. 9). For a given fluorophore in a bead, the triplet state population can be manipulated by doping the bead with a quencher that promotes $k_{ISC}$ or $k_T$ (see FIG. 3). By doping the beads with several distinct levels of quencher concentration, different fluorescence changes will result when going from one mode of excitation to another. The quencher concentration in the beads thus offers an additional parameter/dimension by which the beads can be characterised and by which the beads are identifiable using fluorescence read-out by FACS. A successful implementation of concept I along this strategy, has the potential to increase the number of simultaneous assays by an order of magnitude.

As an alternative to the latter fluorescence bead-based approach, fluorescence bar coding can be achieved by labelling of the particles (for instance polystyrene beads, cells, or lipid vesicles) on their surfaces. Due to a process (for instance a binding event), affecting one or several of the molecules to which the different fluorophores have been labelled, or influencing the interaction between these molecules, a change in the triplet state properties (or in any other photo-induced transient state) of one or several of the fluorescent molecules on the surface can be generated. By use of the same excitation procedure as in the latter fluorescence bead-based approach, exciting the beads in at least two different modes while they are flowed through the FACS apparatus, where at least one characteristic parameter of the pulse ($t_{exc}$, $t_{dark}$, $I_{exc}$, polarisation, and pulse shape in time and space) is different between the modes, the characteristics (population and relaxation time) of the triplet state (or any other photo-induced transient state) can be determined from the difference in the fluorescence intensity generated in the different modes. With this approach, the identification of the investigated particles can possibly be maintained, while at the same time possible interactions influencing one or several of the fluorescently marked molecules, or their internal interactions, can be detected. The same excitation procedure can also be applied in a parallel fashion, with simultaneous excitation of a matrix of beads, located for instance in the wells of a micro-well plate.

An example of a specific embodiment of the invention is summarized in the data presented in FIG. 14. In a confocal, epi-illuminated FCS instrument, similar to previously used FCS instrumental arrangements (Widengren et al, *J. Phys. Chem* (1995), 99, P. 13368) (FIG. 14A), with an added acousto-optic modulator, modulating the intensity of the laser excitation in time, rectangular pulse trains were applied to excite Rhodamine 6G fluorophore molecules in aqueous solutions, containing varying amounts of potassium iodide (KI). For the pulse trains, $t_{exc}$, $t_{dark}$, and $I_{exc}$ were varied from one pulse train to the next. The average fluorescence intensity from the confocal detection volume during the excitation periods, normalised with the average intensity from the same volume under continuous excitation with the same excitation intensity, $\overline{F}_{norm}$, was detected and calculated for each pulse train. In FIG. 14B, the variation of $\overline{F}_{norm}$ with $t_{exc}$ and the period time ($t_{exc}+t_{dark}$) is shown for a Rh6G solution containing 4 mM KI, exposed to a laser excitation of 120 μW (within the excitation pulses). Calculated values of $F_{norm}$, based on a three state model (FIG. 3) for R-h6G, and assuming the excitation intensity within the detection volume to have a Gaussian-Lorentzian distribution, were fitted to the experimental values of $\overline{F}_{norm}$ by variation of $k_{ISC}$ and $k_T$. In this non-linear least squares minimization-based fitting (Levenberg Marquart) the obtained parameter values ($k_{ISC}=11\times10^6$ s$^{-1}$, $k_T=0.6\times10^6$ s$^{-1}$) are well in agreement with those extracted by FCS (in the same setup, but at CW excitation). The $k_{ISC}$ parameters determined by the modulation approach were found to increase linearly with increasing K' concentrations. Thus, from the recorded mean fluorescence intensity, by use of modulated excitation, but without using the time resolution of the detection, reliable triplet state parameters could be extracted. The procedure can be performed on a parallel scale, essentially by replacing the avalanche diode detection used here by for instance a CCD camera.

The invention claimed is:

1. A spectroscopic method for measuring and analysing intensities of fluorescent molecules excited by an energy pulse, comprising the steps of:
a) generating a transient state build-up in the fluorescent molecules by means of an excitation pulse, within which pulse repetitive excitation-emission cycles are induced in the fluorescent molecules between their ground, typically singlet ($S_0$), and excited, typically singlet ($S_1$), states, with transition from $S_1$ to the transient state,
b) relaxing of population of the transient state by transition back to $S_0$ in a time period after the excitation pulse,
c) determining the transient state population by recording the fluorescence, characterised by
varying pulse characteristics from one sequence of pulses to the next, circumventing the need for time-resolution in the detection.

2. The method according to claim 1, characterised by pulse characteristics are any one of following parameters: pulse duration, duration between pulses, pulse shape in time and space, polarisation, wavelength, and excitation intensity within the pulses, so as to allow for variation of the extent and kinetics of accumulation of the transient state within the fluorescent molecules.

3. The method according to claim 1, wherein determination of the transient state properties, including its population and rates of population and de-population, is made by recording the average fluorescence intensity over time within at least one wavelength interval during each pulse sequence.

4. The method according to claim 1, wherein the generated transient state including, in addition to triplet states, T, any photo-induced non- or weakly fluorescent state, including photo-isomerised states or photo-ionised states.

5. The method according to claim 4, characterised by the generated transient state further comprising states which can emit fluorescence in another wavelength range as that in which the fluorescent molecules emit at the beginning of the excitation pulse.

6. The method according to claim 1, wherein the transient state, including a triplet state, having a low probability per excitation-emission cycle to be generated, and having slow relaxation back to the ground initial state as compared to $S_1$-to-$S_0$ relaxation.

7. The method according to claim 1, wherein varying the length of the excitation pulse within an interval covering lengths long enough for the transient state accumulation to reach a steady-state and lengths short enough to yield only minor transient state accumulation during the excitation pulse.

8. The method according to claim 7, characterised by the excitation pulse length is considered short or long in relation to the monitored relaxation time of the triplet state or the monitored relaxation time of the transient state.

9. The method according to claim 1, wherein choosing long enough time durations between the excitation pulses so as to allow the transient states to relax back, or short enough to induce a cumulative increase of the transient state population with an increasing number of pulses within a pulse sequence.

10. The method according to claim 9, characterised by the time duration between the pulses being considered short or long in relation to more than one multiple of the monitored relaxation time of the triplet state, or of the relaxation time of the transient state.

11. The method according to claim 1, comprising adding an inducer/quencher enhancing at least one of the intersystem-crossing rate and the T-$S_0$ relaxation rate in order to influence the fluorescence following excitation.

12. The method according to claim 11, characterised by choosing the quencher in order to influence the fluorescence from different fluorescent molecule types differently depending on whether the intersystem crossing or the T-$S_0$ relaxation is preferentially enhanced.

13. The method according to claim 11, wherein
addition of any other compound influencing the transition rates to or from a transient state other than a triplet state, effective via collisional interactions and changes in the viscosity, polarity and conductivity of the medium surrounding the fluorescent molecules.

14. The method according to claim 11, wherein
the fluorescent molecules affected by the quencher being parts in a fluorescence resonance energy transfer (FRET) system, where the depopulation rate is promoted over the formation rate for the transient state in the donor fluorescent molecule(s), and vice versa for the acceptor fluorescent molecule(s).

15. The method according to claim 14, characterised by
the transient state is a triplet state and the formation and depopulation rates are intersystem crossing to the triplet state and $T$-$S_0$ relaxation, respectively.

16. The method according to claim 1, comprising
applying light-induced modification of the effective rates of transition to and from the transient state, by effecting excitation to higher triplet and singlet states.

17. The method according to claim 16, characterised by
the light-induced modification of the said transition rates is effected by at least one additional radiation field, shifted in time and wavelength, but overlapping in space with the excitation energy pulse described.

18. The method according to claim 16, wherein
the light-induced modification is generated as pulse sequences in time, with the possibility of varying the pulse characteristics and the delay in time between pulse trains from the excitation and radiation fields, as well as their respective excitation wavelengths.

19. The method according to claim 16, wherein
at least one additional level of modulation of the pulses within the pulse sequences, such that the pulses within the said pulse sequences of the excitation field and the additional radiation field(s) have a superimposed modulation, generating additional pulse trains with a higher frequency within these pulses, the pulses within the additional pulse trains also being modulated generating a second additional level of pulse trains within the pulses of the first additional pulse trains.

20. The method according to claim 16, further comprising:
varying the pulse characteristics of and the delay in time between all additional superimposed pulse trains from the different fields of excitation and radiation.

21. The method according to claim 1, wherein
adding a feed-back control adapting the pulse characteristics of the excitation field and that of at least one additional radiation field, and
adding time delays between the pulse sequences of said fields, based on the transient state characteristics, with the purpose of maximising the response in transient state characteristics from changes in transient state rate parameters originating from changes in the microenvironment around the fluorescent molecules, or a molecular interaction taking place.

22. The method according to claim 21, characterised by
using said feed-back control to maintain a defined, clamped, set of transient state parameters, and using the necessary adaptation in one or several of the parameters defining the pulse characteristics of the pulse trains as read-out.

23. The method according to claim 1, comprising
analysing fluorescence-coded polymer beads, where the beads in addition to content of fluorescent molecules and their emission wavelengths are separable with respect to the extent to which the beads are doped with a triplet-state quencher/inducer.

24. The method according to claim 1, comprising
analysing fluorescence-coded particles, including beads, cells and lipid vesicles, which have at least some of their fluorescent molecules attached to their surfaces, and where the fluorescent properties of one or several of the fluorescent molecules can change as a consequence of an interaction taking place on the surface.

25. The method according to claim 1, wherein
the excitation energy pulse and possible additional radiation fields being generated by at least one focused laser beam, whereby the excitation intensities and energies of the pulses can be concentrated to a small area or volume generating sufficient excitation rates for transient state build-up in the fluorescent molecules without the need of high-intensity excitation means.

26. The method according to claim 1, comprising
monitoring the dwell time of the fluorescent molecules in an excitation field, by the transient state population as an effect of the number of excitation pulses experienced by the fluorescent molecules during the dwell time.

27. The method according to claim 1, comprising
generating the excitation energy pulse and one or several additional radiation fields by use of patterns of excitation fields, including patterns of excitation fields generated by interference between two or more excitation fields, or by patterned masks in the illumination field, all modulated in time and space.

28. The method according to claim 1, comprising
generating and analysing beating frequencies of the detected fluorescence in space and time, generated by an excitation field and at least one additional radiation field, and influenced by the transient state build-up and kinetics.

29. The method according to claim 27
tuning of the spatial and temporal frequencies of the excitation field and that of the one or several additional radiation fields with respect to the transient state kinetics of the interrogated fluorescent sample such that monitored changes in transient state kinetics generates a larger relative shift in the beating frequencies.

30. The method according to claim 25, wherein
utilising shorter passage times through an excitation field for freely diffusing fluorescent molecules, thereby minimising the extent of photobleaching.

31. The method according to claim 30, characterised by
at least one of the excitation fields comprises a laser beam.

32. The method according to claim 25, wherein
utilising translation of fluorescent molecules with respect to an excitation field, thereby further minimising the extent of photobleaching.

33. The method according to claim 1, wherein
switching between any luminescent state other than a singlet state and a transient non-luminescent or more weakly luminescent state of a fluorescent molecule.

34. The method according to claim 1, wherein
exchanging fluorescent molecules with other entities, including quantum dots or fluorescent nanoparticles, as units to be switched between luminescent and non-luminescent, or more weakly luminescent photo-induced transient states.

35. The method according to claim 1, wherein
combining the described fluorescence recording with simultaneous recording from the fluorescent molecules, or units investigated, of at least one additional luminescence parameter, including fluorescence lifetime, polarization and wavelength, and the same parameters and the intensity extracted from possible delayed fluorescence or phosphorescence, the latter two following repopulation of an excited singlet state and deactivation of a triplet state, respectively.

36. A spectroscopic apparatus for measuring and analysing intensities of fluorescent molecules following excitation, the apparatus comprising:

means for generating a transient state build-up in the fluorescent molecules by means of an excitation pulse, within which pulse typically at least one excitation-emission cycle is induced in the fluorescent molecules between their ground, typically singlet ($S_0$), and excited, typically singlet ($S_1$), states, with transition from the excited state to a long-lived non-fluorescent or weakly fluorescent transient state, recording means for determining the transient state population by recording the fluorescence, and means are provided for varying pulse characteristics from one sequence of pulses to the next so as to circumvent the need of time-resolution in the detection.

37. The apparatus according to claim 36, characterised in that the recording means comprises a detector.

38. The apparatus according to claim 36, wherein
means are adapted to carry out the method of claim 1 in a parallelised manner, including parallelised monitoring of states.

39. The apparatus according to claim 36, comprising
matrices with excitation regimes are applied onto a sample area/volume, which is monitored by wide-field detection.

40. The apparatus according to claim 36, wherein
the means for generating the transient sate build up is implemented in a fluorescence microscope, a fluorescence plate reader, or an instrument for fluorescence-activated cell sorting.

41. The apparatus according to claim 36, wherein
the emitted fluorescence following excitation is subject to a spatial filter, in the image plane by one or several pinholes, or by some other masks variable in time and space.

42. The apparatus according to claim 36, wherein
a sample area is a micro-well or a spot on an array of solid-supported nucleic acids, peptides, or proteins, or a surface of or the interior of a cell, or a biological tissue.

43. The apparatus according to claim 36, wherein
spatial and/or temporal variation of the excitation fields are generated by interference patterns produced from two or more excitation fields, generated by use of laser or light beam modulators/deflectors, based on an acousto-optic principle, by use of masks, or by other means of spatial filtering, all modulated in time and/or in space.

44. The apparatus according to claim 36, wherein
means are provided for periodic excitation with consecutive pulse trains applied to one and the same area/volume, or for several areas/volumes in parallel, where the pulse characteristics in one area/volume are varied from one pulse train to the next.

45. The apparatus according to claim 36, wherein
the at least one excitation field in the plane of a sample is provided by two-photon excitation or an evanescent field following total-internal reflection.

46. The apparatus according to claim 36, wherein
multiple excitation arrays are created by division of the excitation beam, by multiple semi-transparent mirrors, or created by use of gratings, related diffractive optics, or spatial light modulators.

47. The apparatus according to claim 36, wherein
the fluorescence read-out is combined with instrumental means for simultaneous read-out of other fluorescence parameters, including lifetime, polarisation and wavelength, extractable from the fluorescent molecules or units investigated.

* * * * *